(12) United States Patent
Witt et al.

(10) Patent No.: US 10,073,012 B2
(45) Date of Patent: Sep. 11, 2018

(54) DEBRIS FILTER FOR FLUIDIC MEASUREMENT WITH RECESS SIZE DECREASING IN FLUID FLOW DIRECTION

(75) Inventors: Klaus Witt, Waldbronn (DE); Hans-Georg Haertl, Waldbronn (DE)

(73) Assignee: Agilent Technologies, Inc., Santa Clara, CA (US)

(*) Notice: Subject to any disclaimer, the term of this patent is extended or adjusted under 35 U.S.C. 154(b) by 969 days.

(21) Appl. No.: 14/342,714

(22) PCT Filed: Sep. 4, 2011

(86) PCT No.: PCT/EP2011/065244
§ 371 (c)(1),
(2), (4) Date: Jul. 1, 2014

(87) PCT Pub. No.: WO2013/029691
PCT Pub. Date: Mar. 7, 2013

(65) Prior Publication Data
US 2014/0305228 A1    Oct. 16, 2014

(51) Int. Cl.
| | |
|---|---|
| *B01D 35/00* | (2006.01) |
| *G01N 1/20* | (2006.01) |
| *B01D 39/00* | (2006.01) |
| *B01D 39/10* | (2006.01) |
| *B01D 39/14* | (2006.01) |

(52) U.S. Cl.
CPC .............. *G01N 1/20* (2013.01); *B01D 39/00* (2013.01); *B01D 39/10* (2013.01); *B01D 39/14* (2013.01); *B01D 2239/065* (2013.01); *B01D 2239/069* (2013.01); *B01D 2239/1216* (2013.01)

(58) Field of Classification Search
None
See application file for complete search history.

(56) References Cited

U.S. PATENT DOCUMENTS

| | | | |
|---|---|---|---|
| 3,935,111 A | 1/1976 | Bentley | |
| 4,056,476 A * | 11/1977 | Mouwen | A61M 1/3627 139/383 A |
| 4,222,877 A * | 9/1980 | Silva | B01D 24/007 210/411 |
| 5,472,600 A | 12/1995 | Ellefson | |
| 5,476,588 A | 12/1995 | Nagoaka | |

(Continued)

FOREIGN PATENT DOCUMENTS

| | | |
|---|---|---|
| CN | 1033942 A | 7/1989 |
| CN | 101389388 A | 3/2009 |

(Continued)

OTHER PUBLICATIONS

International Search Report and Written Opinion dated Sep. 11, 2013, for corresponding patent application PCT/EP2011/065244 filed Sep. 4, 2011.

(Continued)

*Primary Examiner* — Richard C Gurtowski

(57) ABSTRACT

A filter for filtering debris out of a fluid flowing along a fluid flow direction in a fluidic member of a sample separation device, the filter comprising a plurality of filter structures stacked along the fluid flow direction and each having pores with defined pore size, wherein the defined pore size of the stacked filter structures decreases along the fluid flow direction.

16 Claims, 5 Drawing Sheets

(56) References Cited

U.S. PATENT DOCUMENTS

| | | | |
|---|---|---|---|
| 6,586,585 B1 | 7/2003 | Bastian | |
| 2001/0047966 A1 | 12/2001 | Colpan | |
| 2011/0073539 A1 | 3/2011 | Yotani | |
| 2011/0262325 A1* | 10/2011 | Iwanaga | A61L 9/00 |
| | | | 423/210 |
| 2013/0001145 A1 | 1/2013 | Yin et al. | |

FOREIGN PATENT DOCUMENTS

| | | |
|---|---|---|
| CN | 101668580 A | 3/2010 |
| CN | 102131737 A | 7/2011 |
| DE | 3719415 A1 | 12/1988 |
| EP | 0266204 A2 | 5/1988 |
| EP | 0494742 A1 | 1/1992 |
| JP | 2003080013 A | 3/2003 |
| WO | 9610747 A1 | 4/1996 |
| WO | 2010022019 A1 | 2/2010 |
| WO | 2011090978 A1 | 7/2011 |

OTHER PUBLICATIONS

Database WPI, Week 200370, Thomson Scientific, Long, GB; AN 2003-735453 XP002697536, & JP 2003080013 A Mar. 18, 2003 abstract.
Chinese Office action dated Feb. 4, 2017 from related Chinese Application No. 201180073244.7.

* cited by examiner

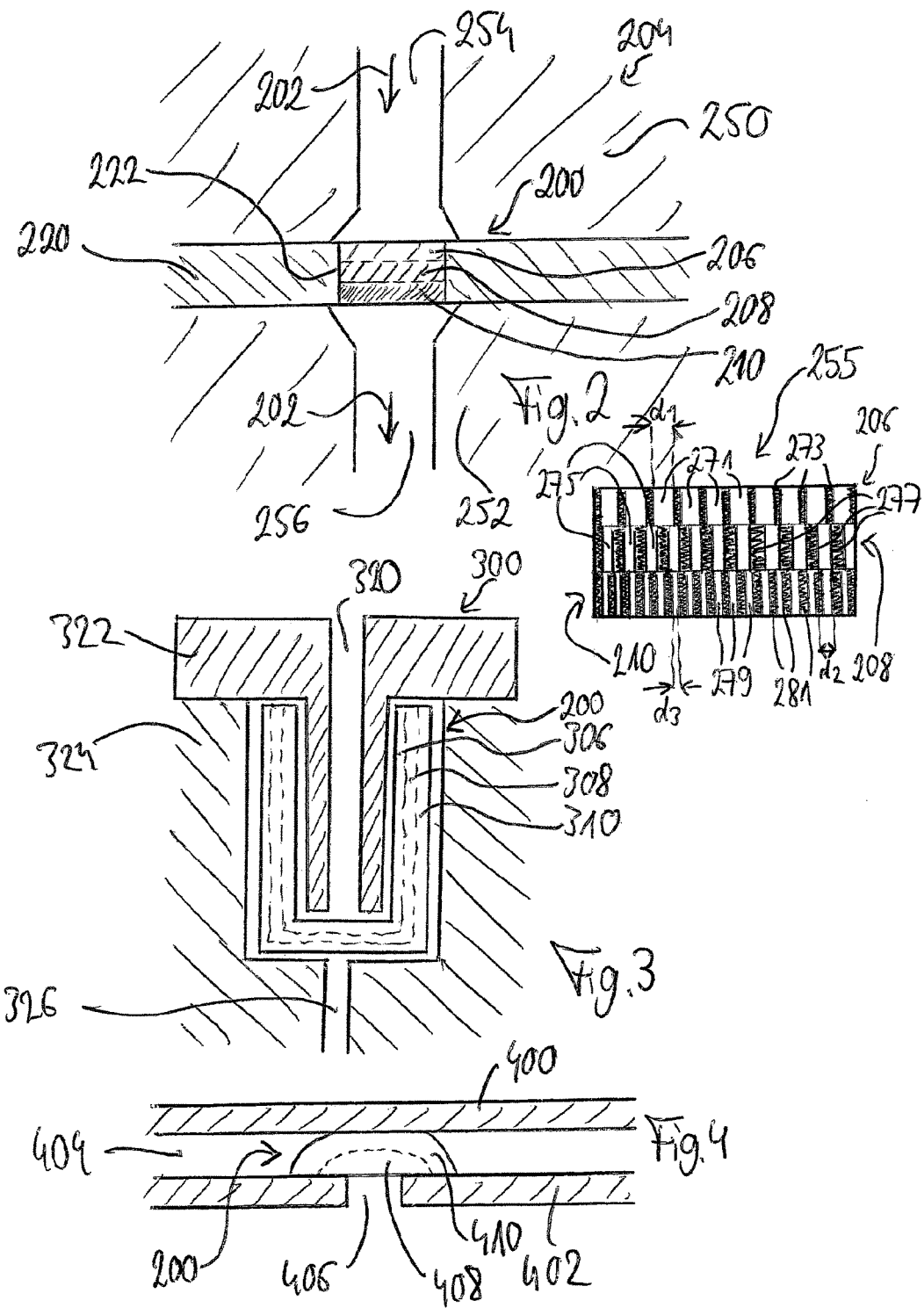

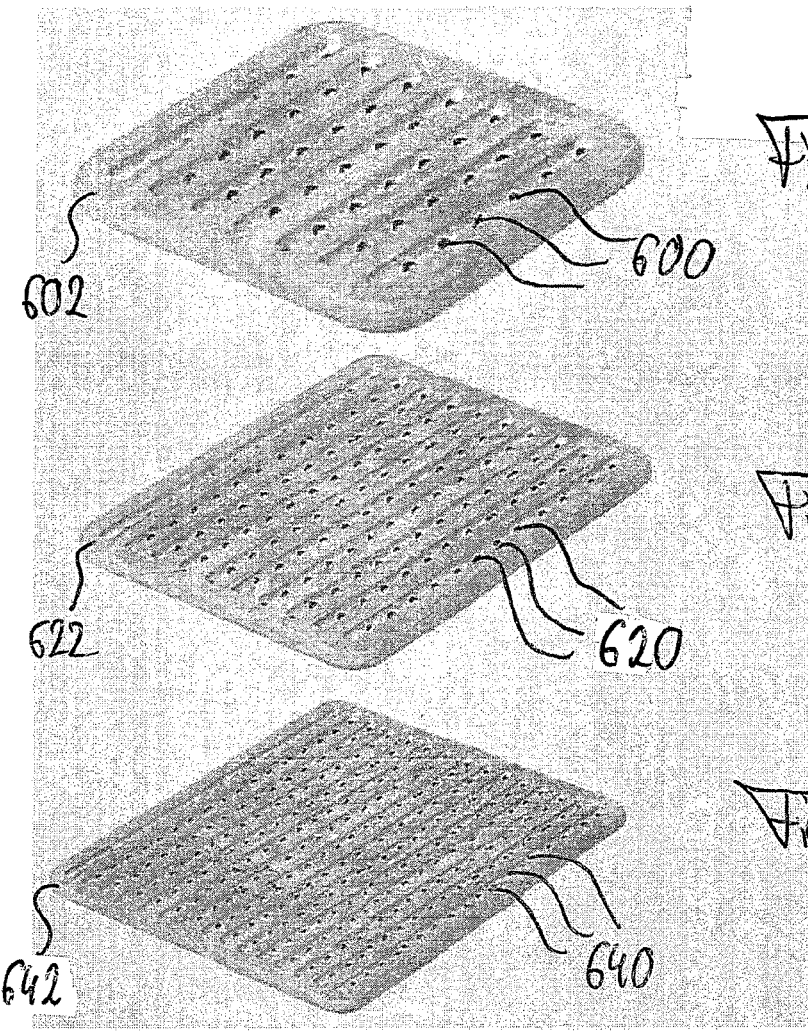
Fig. 6A
Fig. 6B
Fig. 6C
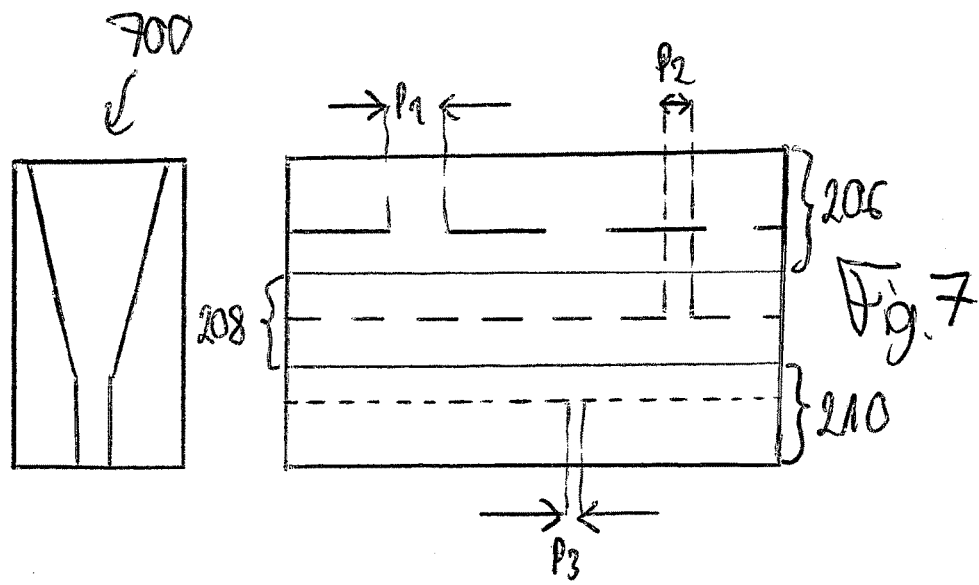
Fig. 7

DEBRIS FILTER FOR FLUIDIC MEASUREMENT WITH RECESS SIZE DECREASING IN FLUID FLOW DIRECTION

RELATED APPLICATIONS

This application is the national stage of International Application No. PCT/EP2011/065244, filed Sep. 4, 2011, titled "DEBRIS FILTER FOR FLUIDIC MEASUREMENT WITH RECESS SIZE DECREASING IN FLUID FLOW DIRECTION," the content of which is incorporated herein by reference in its entirety.

BACKGROUND ART

The present invention relates to a filter, a fluidic member, a sample separation device, and a method of manufacturing a filter.

In liquid chromatography, a fluidic sample and an eluent (liquid mobile phase) may be pumped, by a piston pump, through conduits and a column in which separation of sample components takes place. In a sample loop, the sample may be injected into a fluidic path by a mechanically drivable needle. The drivable needle is controllable to be moved out of a seat of the sample loop into a vial to receive a fluid and back from the vial into the seat. The column may comprise a material which is capable of separating different components of the fluidic analyte. Such a material, so-called beads, which may comprise silica gel, may be filled into a column tube which may be connected downstream to other components, such as a detector, a fractioner, a waste, etc., by conduits.

In such and other fluidic measurement devices, debris can be unintentionally introduced in the processed fluid, for instance due to abrasion of a seal in a piston chamber of a pump, abrasion of a rotatable fluidic valve during switching, solid matter in the matrix of the sample, etc. Hence, filters may be introduced at certain positions within the flow path. Specific filters called frits may be made of a sintered material having pores or internal gaps allowing fluid to pass the filter but preventing debris particles from passing the filter.

EP 0,231,432, WO 93/11862, U.S. Pat. Nos. 5,304,487 5,985,164, US 2007/199877 disclose various filter concepts.

U.S. Pat. No. 7,645,383 discloses a microstructured filter having an inlet for unfiltered fluid, an outlet for filtered fluid, a plurality of projections, which form at least one row in a mutually juxtaposed relationship across the filter, that project out of a base plate and are an integral component of the base plate, a plurality of passages between the projections, and a cover plate which is securable to the base plate to cover the projections and the passages. The passages form a plurality of through paths from the inlet to the outlet. The inlet includes an elongate inlet slot for the unfiltered fluid that extends over approximately the entire filter width and is approximately as high as the projection on the outlet side of the filter.

US 2001/047966 discloses a method of isolating cell components, such as nucleic acids, from natural sources by filtering a sample of the digested natural sources such as cells or cell fragments. The method is characterized in that the sample is passed through a filter, the pore size of which decreases in the direction of flow of the sample through the filter.

However, conventional filters may suffer from clogging or plugging when a certain amount of debris has been loaded onto the filter. This may result in an undesired blockage of fluid flow. In case of partly blockage the pressure drop may increase to a level, at which such filters may break due to mechanical forces.

DISCLOSURE

It is an object of the invention to provide a filter which is less prone to clogging or plugging, while low volume is invested. Another object of this invention is to provide a rigid or strong structure, which is susceptible to a certain clogging. Yet another object is to provide a filter which is constructed to support easy cleaning.

According to an exemplary embodiment of the present invention, a filter for filtering debris out of a fluid flowing along a fluid flow direction in a fluidic member of a sample separation device is provided, wherein the filter comprises a plurality of filter structures (such as layers or non-planar structures such as cup-shaped elements) stacked along the fluid flow direction and each having pores with defined pore size (i.e. the pores in any of the filter structure layers or the like may be identical or do not differ by more than manufacturing tolerances, particularly do not differ by more than 5-10% from an average value, more particularly do not differ by more than 2% from an average value). The defined pore size of the stacked filter structures decreases along the fluid flow direction.

According to another exemplary embodiment, a fluidic member for processing a fluid flowing along a fluid flow direction in a sample separation device is provided, the fluidic member comprising a fluid inlet at which the fluid to be processed is supplied, a processing unit configured for processing the fluid supplied at the fluid inlet, a fluid outlet at which the fluid is supplied after processing by the processing unit, and a filter having the above mentioned features for filtering debris out of the fluid and being arranged between the fluid inlet and the fluid outlet.

According to still another exemplary embodiment, a sample separation device for separating compounds of a sample fluid in a mobile phase is provided, the sample separation device comprising a mobile phase drive, particularly a pumping system, configured to drive the mobile phase through the sample separation device, a separation unit, particularly a chromatographic column, configured for separating compounds of the sample fluid in the mobile phase, and a filter having the above mentioned features for filtering debris out of at least one of the sample fluid and the mobile phase.

According to yet another exemplary embodiment, a method of manufacturing a filter for filtering debris out of a fluid flowing along a fluid flow direction in a fluidic member of a sample separation device is provided, wherein the method comprises forming pores with defined pore size in each of a plurality of filter structures (such as filter structure layers), and stacking the plurality of filter structures along the fluid flow direction so that the defined pore size of the stacked filter structures decreases along the fluid flow direction.

In the context of this application, the term "filter" may particularly denote a physical structure which is capable of preventing particles above a certain size from passing the filter, whereas particles below this size will be able to flow through this filter. The cut-off size of particles being enabled to pass the filter or not is defined by the pore sizes.

In the context of this application, the term "filter structure", particularly "filter structure layer", may particularly denote a physical component forming part of the filter, i.e. functionally contributing to the entire filter function. Each filter structure, particularly filter structure layer, is characterized by a defined pore size, wherein the filter structure, particularly filter structure layer, comprises a plurality, particularly at least 100, pores which have basically the same size. Therefore, no broad size distribution is present in a filter structure, but in contrast to this the pore sizes of different pores of one and the same filter structure layer should be identical within manufacturing tolerances and other tolerances of the respective filter structure.

In the context of this application, the term "pore" may particularly denote any void or recess within a solid matrix of a respective filter structure, particularly filter structure layer, that conducts in the axis of flow, which then allows debris particles having a size smaller than a respective pore size to pass through the pore, whereas debris particles having a size larger than a respective pore size may be trapped at the pore. At least a part of pores of adjacent filter structures should be in fluid communication to one another so as to form a continuous fluidic path through the filter allowing the fluid to pass the filter. The size of the pore may particularly denote the area or diameter of the pore in a fluid flow direction and may be constant (or may vary) along the fluid flow direction in the respective filter structure. The size of the pores may be a dimension of the pores of a filter stack which dimension defines the cut-off dimension of debris particles flowing through the pores. Pores may be straight structures or may have a more complex structure (such as a bent or an arcuate trajectory), but always have a defined size in terms of a cut-off size distinguishing between debris passing the pore and debris being stuck in the pore. Measurement of a pore size may be done for instance by inspecting an electron microscopy image or phenomenologically by conducting fluid containing debris of a defined size through the pore and determining the largest size of debris particles which are still capable of passing through the pores of a certain size.

In the context of this application, the term "stacked" may particularly denote that the various filter structures, particularly filter structure layers, are connected to one another and arranged in a certain order so as to achieve the continuous or stepwise reduction of the pore size along the fluid flow direction. To improve rigidity or strength such stacked layers are affixed or mounted to each other to hold against some pressure drop even when debris has clogged a substantial portion of flow paths across the filter.

In the context of this application, the term "debris" may particularly denote any particles forming a solid state impurity in a fluid such as a fluidic sample under analysis. Although the dimensions of the debris particles may differ according to their origin or different exemplary embodiments of the invention, a preferred embodiment of the invention relates to filtering of a fluid in a liquid chromatography system in which debris may occur from abrasion of a switchable fluidic valve, a piston reciprocating in a piston chamber of a high pressure pump, solid matter in the matrix of the sample, etc. Such technical impurities can be unintentionally introduced in the fluid and can then be removed from the pumped fluid by the filter.

In the context of this application, the term "fluid" may particularly denote any liquid, any gas, any mixture of liquid and gas, optionally comprising solid particles such as the debris. Particularly, also analytes in liquid chromatography are not necessarily liquids, but can be dissolved or undissolved solids or dissolved gases.

In the context of this application, the term "fluid flow direction" may particularly denote an actual or target direction along which the fluid carrying the debris is transported along a fluidic path during operation, particularly driven by drive units such as a drive pump. Therefore, the term fluid flow direction relates to an ordinary pumping direction of the device. In case of a back-flush condition the actual fluid may be flowing against the nominal "fluid flow direction".

According to an exemplary embodiment of the invention, a filter is provided which is capable of providing a filter function for filtering debris out of a flowing fluid with a high performance and a deterministic behavior. Firstly, the precise definition of the pore size for each of the stacked filter structures allows for a high reproducibility when filtering fluid. Therefore, statistical variations of a filter performance among different filters can be ruled out to a large extent in view of the defined pore size arrangement in the filter and the resulting deterministic filter characteristic. Moreover, the fact that the pore sizes become smaller the further the fluid has flown downstream through the filter has the advantage that a fraction-wise filtering of the debris (i.e. sorted with regard to size of debris particles) can be obtained. The largest particles of the debris will already be filtered out in a filter structure being relative early in the stacked path of filter structures. Smaller debris particles will be filtered out of the fluid only at a filter structure more downstream in the sequence of stacked filter structures. By this sorting characteristic it is possible to prevent the undesired effect of conventional filters that an occlusion of pores occurs already at an upstream section of a filter because here basically all debris of all sizes is already trapped in the filter. Another advantage of the filter according to an exemplary embodiment of the invention is that it can be properly back flushed in order to clean it from a load of debris accumulated during a previous filtering procedure. By a simple back flushing flow pulse, the largest particles of debris will easily find a way out of the pore network of the filter because these particles have been caught in the filter already at an upstream end in relation to the fluid flow direction. For smaller debris particles, removal by back flushing is also an easy task, because after having left the narrower filter structure where the respective debris has been trapped, the debris will find an easy way out through the sequentially connected larger pores of adjacent or other filter structure layers of the filter. Thus, the combination of the defined pore dimensions on the one hand and the stepwise or quasi-continuous decrease of the size of the pores of different filter structures along a fluid flow direction allows to obtain the mentioned technical advantages. In the path or direction of a moving particle during back flush it feels like moving out of a funnel reversely.

In the following, further exemplary embodiments of the filter will be explained. However, these embodiments also apply to the fluidic member, the sample separation device, and the method of manufacturing a filter.

In an embodiment, the plurality of filter structure layers are sheets connected to one another at main surfaces of adjacent ones of the sheets. Such sheets may be made of a metallic or polymer material. Such a sheet may be a thin plate, for instance disk-shaped, stripe-shaped, or squared. The two respective main surfaces of a sheet are those opposing surfaces of the sheet which have the largest surface areas. By connecting such sheets to one another in a temporary or in a permanent way, a filter is obtained which has precisely defined characteristics and which on the other hand can be manufactured easily, yet still it is a stiff/rigid structure especially in the direction of flow. A permanent connection may for instance be achieved by sintering or thermal bonding or even by adhering the individual sheets to one another using an appropriate glue. A temporary connection may be achieved by arranging a stack of sheets within a clamping element which clamps the sheets against one another. This can be supported by structured elements on the surface (such as a hook and loop fastener).

In an embodiment, the plurality of filter structure layers are connected to one another as an integrally formed stack. The formation of an integral stack, i.e. an inseparable piece of the multiple filter structure layers renders the filter particularly suitable for high pressure applications such as required in liquid chromatography applications where pressure values of for instance 1200 bar may occur. Due to the integral formation, the filter is very robust and may withstand such high pressures and connected forces.

In an embodiment, at least a part of the plurality of filter structure layers has pores with one defined uniform pore size. The term "defined uniform pore size" may particularly denote that only a single pore size is assigned to the pores of one of the filter structure layers. Therefore, all pores of this filter structure layer will have the defined uniform pore size which will only differ with regard to technical tolerances or the like (such as manufacturing tolerances of 5% of the pore size as compared to an arithmetic average pore size). Taking this measure will allow to obtain highly accurate filter properties of the final filter stack.

In an embodiment, the defined pore sizes of the stacked filter structures strictly monotonically decrease along the fluid flow direction. In such an embodiment, each filter structure fulfils the pore size design rule that its pores are larger than the pores of all filter structures located downstream of this filter structure and that its pores are smaller than all pores arranged upstream of this filter structure.

In an embodiment, the defined pore sizes of the stacked filter structures are in a range between about 0.5 μm and about 100 μm, particularly in a range between about 2 μm and about 30 μm. Although each filter structure layer may have a certain dedicated pore size, this pore size may be within these ranges given for this pore size, i.e. from which range the certain pore size can be selected. Certainly, the exact dimension, design goal, of the pores depends on the application of the filter. However, for filters for fluid separation systems operating under high pressure, particularly liquid chromatography separations, the given ranges have turned out to be particularly advantageous. For example, a high pressure pump may produce wear particles, which are polymeric blocks/bricks of a certain minimal size, so the filter pores may be adapted to the problem, or it may be equipped with a filter having relatively small smallest pores in order to filter out any kind of impurities, just to stay on the save side. In contrast to this, if the filter is used as a replacement for a conventional frit at an outlet of a chromatographic separation column, it has to be ensured that the beads in such a column are not flushed out of this column through the filter. Therefore, the pore sizes shall then be smaller than the size of the beads, for instance smaller than 1.8 μm in modern rapid resolution columns, or they may be smaller than 5 μm when larger beads are packed in the column.

In an exemplary embodiment of a filter constituted of three filter structures, a pore size in a first filter structure may be in a range between 5 μm and 30 μm, a pore size in a second filter structure may be in a range between 3 μm and 10 μm, and a pore size in a third filter structure may be in a range between 0.5 μm and 5 μm, with the boundary condition that the pore size in the first filter structure is larger than the pore size in the second filter structure, the latter being in turn larger than the pore size in the third filter structure.

In an embodiment, at least a part of the plurality of filter structures comprises a substrate. A first main surface of the substrate may be provided with a plurality of oblong first grooves extending along a first direction. A second main surface of the substrate opposing the first main surface may be provided with a plurality of oblong second grooves extending along a second direction. The first grooves and the second grooves may have such a depth within the substrate so as to form an array of through holes in the substrate. At each intersection between one of the first grooves and one of the second grooves, a corresponding through hole is formed in the substrate traversing the latter to connect the two opposing main surfaces. The through holes may constitute the pores with the defined pore size. This embodiment is particularly advantageous to guarantee a defined and reproducible pore size for each of the sheets or substrates. At the same time, it can be manufactured with reasonable effort because it requires basically only one mask for patterning the two opposing main surfaces of the substrate to thereby form a two-dimensional arrangement of pores of identical size. Such a patterning may be performed by a combination of lithography and etching, as known by those skilled in the art. By simply etching linear grooves (extending along different spatial directions, i.e. being angled relative to one another) in two opposing surfaces of the substrate with an appropriately chosen depth (which can be adjusted by adjusting the etching chemicals, the etching time, etc.) not only defined dimensions, but also a defined ordered arrangement of pores, for instance in a matrix-like way, can be obtained.

In an embodiment, the first direction is perpendicular to the second direction. Such a perpendicular arrangement of these two directions has the advantage that a corresponding structure can be formed with reasonable effort and with high accuracy and will result in an ordered, matrix-like pattern of pores.

In an embodiment, the first grooves and/or the second grooves have a concave shape in the substrate. Such a concave shape may be achieved by using a isotropic etching procedure. If the concave bottom parts of the grooves are connected to one another to form through-holes, even pores of relatively small dimensions can be manufactured, as compared to non-isotropic etching, which produces trenches having a rectangular cross-section. This can be advantageous for applications in which debris of particularly small sizes shall be filtered out and renders the resulting filter suitable also for microfluidic or nanofluidic applications.

In an embodiment, grooves of different ones of the plurality of filter structure layers differ concerning at least one geometrical parameter, thereby constituting the pores with the different defined pore size in different filter structure layers. By simply adjusting design or process parameters to produce geometrical groove parameters such as groove depth, groove width, distance between different grooves, angular relationship between adjacent and opposing grooves, shape of the trench associated with the grooves and the substrate, etc. it is possible to precisely predict and define a desired pore size distribution.

In an embodiment, the plurality of filter structures comprise mesh wires, wherein different mesh wires have different values of mesh apertures (forming the pores). For example, first mesh wires may extend along a first direction and second mesh wires may extend along a second direction which may differ from the first direction, particularly may be perpendicular to the first direction. The mesh wires may be connected to one another at intersections either by friction, for instance by forming a woven network of the mesh wires.

It is however also possible that the mesh wires are permanently connected to one another at intersections by adhering, thermal bonding, sintering or the like. In this way, various planar meshes of different apertures may be formed by selecting a different distance between adjacent wires and/or by using different wire thicknesses for different filter structures. Then, an arrangement of meshes having different apertures may be stacked over one another and may be connected to one another to thereby form the filter. Such a mesh arrangement may be small in dimension and therefore highly compact and may at the same time provide for a precisely defined pore size in each mesh or filter structure.

In yet another exemplary embodiment, it is possible that the pores are formed in a substrate by a single patterning procedure. For example, a corresponding patterning mask may comprise an arrangement of dots which are removed by lithography and etching to thereby generate through-holes in the substrate to be etched which then form the pores. Pores could be produce by a micro-milling operation like laser ablation. In still another exemplary embodiment, sacrificial structures of defined dimensions may be integrated in a substrate and may later be removed by a selective etching procedure which only removes the sacrificial structures, but not the substrate material. As an example, such sacrificial structures may be nanowires such as carbon nanowires. Other applications from micro- and nanotechnology may be applied as well for forming an ordered pore structure.

In an embodiment, the plurality of filter structures are cup-shaped with different sizes so that the stacked arrangement is formed by interleaving the cup-shaped filter structures of different sizes into one another. The various cups may be dimensioned so as to form a large gap-free cup structure when being connected to one another. The arrangement of cup-shaped filter structures relates to a geometrical configuration in which the filter structures have a bottom wall such as a cylindrical plate. This bottom plate is connected to or integrally formed with a hollow cylindrical structure forming sidewalls of the cup-shaped structure. The provision of the filter structures as cup-shaped has the advantage that multiple cups may be plugged together, the size of the inner cups being smaller than the size of the outer cups. Therefore, a particularly pressure stable arrangement of a filter may be provided. In such an arrangement, the pores of the larger sizes are arranged in the cup-shaped structures with the smaller dimensions. The fluid then flows from an interior of the cups to an exterior of the cups.

In an embodiment, the plurality of filter structures are disk-shaped and are stacked concentrically to form a cylindrical filter. The disk-shaped filter structures may be connected to one another at their main surfaces.

In an embodiment, the filter comprises an annular support structure, wherein the plurality of filter structures are fastened within in a recess in the annular support structure. Such an annular support structure allows to provide the filter in a manageable manner, wherein the surrounding annular structure does not only mechanically support the filter structures but also serves as a mounting provision for mounting the filter member in a device such as a fluid separation system.

In an embodiment, the filter is configured for being resistant against a pressure of more than about 600 bar, particularly of more than about 1000 bar. Particularly, the filter is operable in a pressure range between 400 bar and 1200 bar, more particularly between 800 bar and 1200 bar. Therefore, the filter can be appropriate for modern chromatographic applications.

In the following, further exemplary embodiments of the fluidic member will be explained. However, these embodiments also apply to the filter, the sample separation device, and the method of manufacturing a filter.

In an embodiment, the fluidic member is configured as a separation unit, particularly a chromatographic column, configured for separating compounds of the fluid, wherein the filter is arranged at an inlet and/or at an outlet of the separation unit. A chromatographic separation column needs to be fed, at its inlet, with a pure and debris free fluid. Therefore, the inlet of the separation column can be provided with a filter according to an exemplary embodiment of the invention to replace a conventional frit. Additionally or alternatively, the outlet of the column can be provided with a filter according to an exemplary embodiment of the invention so as to prevent separating beads within the column from being flushed out of the chromatographic column. Such an outlet filter may therefore have the function to inhibit flow of beads through the filter which has an impact on the usable pore sizes. Beads for instance may have a dimension of 1.8 μm so that the pores of the filter at the outlet of the separation column should be smaller than this value.

In an embodiment, the fluidic member is configured as a mobile phase drive, particularly a pumping system, configured to drive the fluid, wherein the filter is arranged at an outlet of the mobile phase drive. In such a high pressure pump, reciprocation of a piston within a seal installed on the piston chamber may result in an abrasion of small particles in the pumping chamber which can then be introduced unintentionally into the fluid. By providing a filter according to an exemplary embodiment at an outlet of such a pumping unit it is possible to prevent debris from entering a connected fluidic path.

In an embodiment, the fluidic member is configured as a sample injector for injecting the fluid in a sample separation path, wherein the sample injector comprises an injection needle and a seat, wherein the injection needle is selectively insertable into the seat for conducting the fluid between the needle and the seat, wherein the injection needle is selectively movable out of the seat, and wherein the filter is arranged at an outlet of the sample injector. Within a sample injector, rotation of a fluidic valve which can be arranged to fluidically couple the sample injector with a path between separation column and mobile phase drive can cause debris to be introduced into the fluid. The sample fluid itself may contain solid particles or macro-species, which may be part of the sample matrix, resulting from previous processing steps. Therefore, providing a filter according to an exemplary embodiment of the invention at such a position is advantageous as well.

In an embodiment, the fluidic member is configured as a metering pump for a sample injector for injecting the fluid in a sample separation path, a detector configured to detect separated compounds of the fluid, a collection unit configured to collect separated compounds of the fluid, a degassing apparatus for degassing the fluid, and/or a piston pump having a piston chamber and a piston configured for reciprocating within the piston chamber. Even in a metering pump, a high pressure can be generated, and debris may be formed by abrasion procedures or frictional procedures. Therefore, provision of a filter according to an exemplary embodiment of the invention at such a metering pump or syringe is advantageous.

In an embodiment, the fluidic member comprises a back flush unit configured for back flushing the filter, for instance periodically or occasionally when loaded with debris. The back flush unit may be configured for flushing the loaded filter with flush fluid flowing opposite to the fluid flow direction. It is a particularly advantage of embodiments of the invention that the filter can be cleaned efficiently by back flushing, i.e. by pumping a fluid pulse through it in a direction opposing to the fluid flow direction. Due to the arrangement of the stacked filter structure layers with pore sizes decreasing in fluid flow direction, the back flushing flushes the trapped debris in a direction in which the debris experiences successively increasing pores, thereby allowing to efficiently clean the filter, in contrast to conventional filters, e.g. built from frit structures.

In the following, further exemplary embodiments of the sample separation device will be explained. However, these embodiments also apply to the filter, the fluidic member, and the method of manufacturing a filter.

In an embodiment, the fluid separation device is configured as at least one of the group consisting of an autosampler device, a fractioner device, a measurement device for performing a measurement in a coupled measurement environment, a measurement device for measuring at least one physical, chemical or biological parameter, a measurement device for performing a measurement of a fluidic sample, a sensor device, a device for chemical, biological and/or pharmaceutical analysis, and a chromatography device (such as a liquid chromatography device or a gas chromatography device).

The fluid separation device may comprise a pump configured for pumping fluid through the system. The fluid may be sucked from a vial into the needle and from there to a capillary. As a pump, a piston pump, a peristaltic pump, a centrifugal pump, a membrane pump, etc., may be implemented.

The fluid separation device may comprise a sample loop for handling a fluidic sample. Such a sample loop may be part of a liquid chromatography apparatus and may allow to inject a sample into the sample loop via the needle at an end portion of a capillary which can be pivoted from the seat of the sample loop to immerse into a fluid container. After having taken up the fluid, the needle can be moved back into the seat so that the injected fluid can be introduced via the sample loop onto a chromatographic column for fluid separation. Such a fluid separation may then be performed by separately releasing different fractions of a sample trapped on the chromatographic column by running a gradient during which a solvent with varying composition may be conducted through the chromatographic column. Exemplary embodiments may hence be implemented in a sample injector module of a liquid chromatography apparatus which sample injector module may take up a sample from a fluid container and may inject such a sample in a conduit for supply to a separation column. During this procedure, the sample may be compressed from, for instance, normal pressure to a higher pressure of, for instance several hundred bars or even 1000 bar and more. An autosampler may automatically inject a sample from the vial into a sample loop. A tip or needle of the autosampler may dip into a fluid container, may suck fluid into the capillary and may then drive back into a seat of a sample loop to then, for instance via a switchable fluidic valve, inject the fluid towards a sample separation section of the liquid chromatography apparatus.

In an embodiment, the fluid separation device may comprise or may be configured as an autosampler for injecting a fluidic sample in an apparatus being in fluid communication with the capillary. Such an autosampler may be a device or module which, in an automatic manner, allows to handle fluid in a specific manner, for instance in accordance with a dedicated mechanism of controlling different vials so that a specific sample composition may be adjusted.

In an embodiment, the above mentioned apparatus served by the autosampler may be a chromatographic column. Therefore, the autosampler may take up a sample and may inject the sample towards a chromatographic column for sample separation.

The fluid separation device may include or cooperate with a processing element (such as a chromatographic column) filled with a separating material. Such a separating material which may also be denoted as a stationary phase may be any material which allows an adjustable degree of interaction with a sample so as to be capable of separating different components of such a sample. The separating material may be a liquid chromatography column filling material or packing material comprising at least one of the group consisting of polystyrene, zeolite, polyvinylalcohol, polytetrafluorethylene, glass, polymeric powder, silicon dioxide, and silica gel, or any of above with chemically modified (coated, capped etc) surface. However, any packing material can be used which has material properties allowing an analyte passing through this material to be separated into different components, for instance due to different kinds of interactions or affinities between the packing material and fractions of the analyte.

At least a part of the processing element may be filled with a fluid separating material, wherein the fluid separating material may comprise beads having a size in the range of essentially 1 μm to essentially 50 μm. Thus, these beads may be small particles which may be filled inside the separation section of the microfluidic device. The beads may have pores having a size in the range of essentially 0.01 μm to essentially 0.2 μm. The fluidic sample may be passed through the pores, wherein an interaction may occur between the fluidic sample and the pores.

The fluid separation device may be configured for separating components of the sample. When a mobile phase including a fluidic sample passes through the fluidic device, for instance with a high pressure, the interaction between a filling of the column and the fluidic sample may allow for separating different components of the sample, as performed in a liquid chromatography device.

However, the analysis system may also be configured as a fluid purification system for purifying the fluidic sample. By spatially separating different fractions of the fluidic sample, a multi-component sample may be purified, for instance a protein solution. When a protein solution has been prepared in a biochemical lab, it may still comprise a plurality of components. If, for instance, only a single protein of this multi-component liquid is of interest, the sample may be forced to pass the columns. Due to the different interaction of the different protein fractions with the filling of the column, the different samples may be distinguished, and one sample or band of material may be selectively isolated as a purified sample.

As an alternative to a liquid mobile phase, a gaseous mobile phase or a mobile phase including solid particles may be processed using the fluid separation device. Also materials being mixtures of different phases (solid, liquid, gaseous) may be processed using exemplary embodiments. The fluid separation device may be configured to conduct the mobile phase through the system with a high pressure, particularly of at least 600 bar, more particularly of at least 1200 bar.

The analysis system may be configured as a microfluidic device. The term "microfluidic device" may particularly denote a fluidic device as described herein which allows to convey fluid through microchannels having a dimension in the order of magnitude of less than 500 µm, particularly less than 200 µm, more particularly less than 100 µm or less than 50 µm or less. The analysis system may also be configured as a nanofluidic device. The term "nanofluidic device" may particularly denote a fluidic device as described herein which allows to convey fluid through nanochannels with a flow rate of less than 100 nl/min, particularly of less than 10 nl/min.

A multi-way switching valve may be provided for selectively routing a fluid input flow to the valve to one of more alternate output flows from the valve. Such a rotary valve may direct fluid flow by rotating a valve rotor element to discrete angular positions relative to a stationary valve stator element. A dual rotary valve provides two valves in one valve body, both simultaneously operated by the positioning of the valve rotor. Such rotary switching valves may be used, for example, in HPLC and other analytical methods to selectively direct a flow stream of one or more fluids along alternate paths to an analytical device or containment vessel.

BRIEF DESCRIPTION OF DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

FIG. 2 shows a fluidic member in which a cylindrical filter mounted in a recess of a support ring is provided for filtering debris out of a liquid.

FIG. 3 illustrates a fluidic member having a cup-shaped filter according to another exemplary embodiment of the invention.

FIG. 4 illustrates a fluidic path in which a pellet-shaped filter according to another exemplary embodiment of the invention is implemented.

FIG. 6A shows a first micro-patterned sheet, FIG. 6B shows a second micro-patterned sheet and FIG. 6C shows a third micro-patterned sheet, the sheets being made of a metallic material and providing different pore sizes as a basis for a filter according to an exemplary embodiment of the invention.

FIG. 7 shows a filter having three filter structures with different pore sizes resulting in a funnel-like filtering characteristic according to an exemplary embodiment of the invention.

Figure 1:
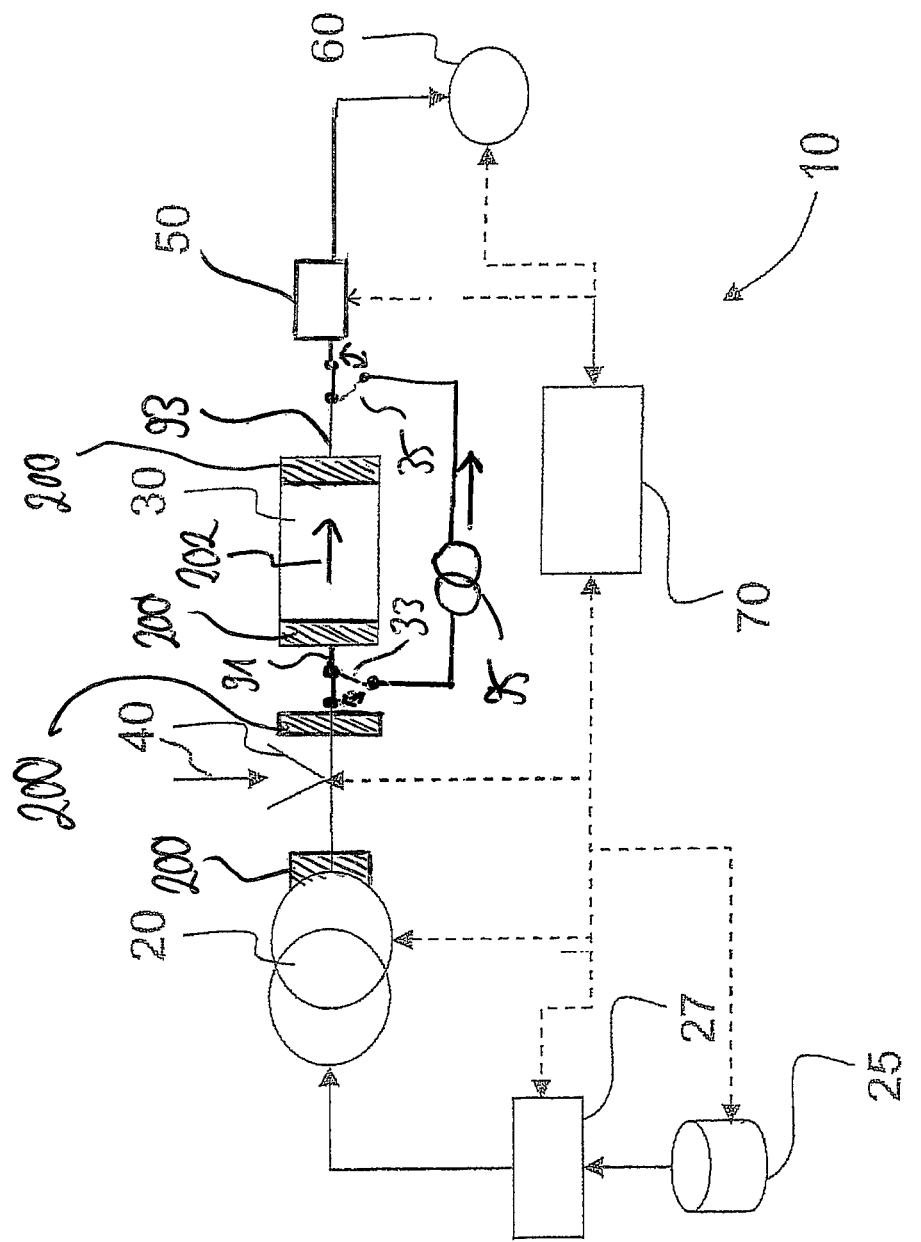
FIG. 1 shows a liquid separation device, in accordance with embodiments of the present invention, e.g. used in high performance liquid chromatography (HPLC).

The illustration in the drawing is schematically.

Embodiments of the invention relate to the filtering of liquid in a three-dimensional structure, particularly implementing a gradually decreasing pore-size in a designed filter. Before exemplary embodiments of the invention will be explained in detail, some basic considerations of the present inventor will be summarized based on which exemplary embodiments of the invention have been developed.

In gradient Liquid Chromatography (LC) systems often there is a requirement to have both dispensing of clean liquids, while pumping against pressure and still having lowest possible delay volume. Modern UHPLC-systems nowadays have ever increasing requirements. In the interest to increase peak capacity (total number of peaks per time interval) several parameters may be optimized such as smaller size of packing material, smaller columns, faster linear speed of solutes during separation, faster compositional gradients, longer separation beds. While on one hand it increases the need for higher pressures, on the other hand it requires less and less total flow. In a scheme of very reduced flow any residual volume in the flow stream becomes more significant, often already limiting performance of the LC system. Using piston pumps for driving fluid against pressure very commonly produces seal wear, which at the end may spoil the separation column. Even a kind of guard-frit may clog early, when used upstream the column to protect the valuable piece. Cost of ownership is increased due to interruption of the analytical use or limitation in robustness. To clear out dirt and debris from the flowing liquid one could use filter paper, but high pressures will easily break these. For a long time it has been common to add filter frits somewhere at the outlet of pumping systems. These filters are often produced as a block of compacted grains, which hold together strongly. Filter frits are random structures, but come in all kinds of sizes.

Now intending to reduce the volume, one may go by diameter and/or thickness, but both have their critical disadvantage. Reducing the diameter also reduces the area on which dirt particles can be collected. Reducing thickness of a frit structure increases the random risk to have one large pore open, which allows bigger debris or particle to sneak through.

A common problem of sieves, or fabric mesh structures is the point of limited capacity. Dirt piles up on the filter area, which soon may collapse under pressure and immediately blocks the flow. In such a case the force will rise rapidly, which then results in a rupture of the mesh. In such a case the collected dirt will suddenly spill down the flow path, eventually resulting in severe damage of downstream components.

In an embodiment of the invention, it is possible to gradually decrease pore-size in a designed three-dimensional structure which works in both dimensions: A) On one hand it is possible to have a defined and homogeneous pores size and a minimum pore size can be exactly matched to the maximum allowed particles so that it is not necessary that the thickness randomizes the pores in series. B) On the other hand there is plenty of space to store the debris (not just the top area is a work space, but due to the three-dimensional structure it is possible to keep much more dirt in the filter before pressure rises.

Moreover, exemplary embodiments of the invention have the additional advantages that dirt and debris is sorted before it hits the adequate sieve layer, between the individual layers there is a radial flow path which may divert the flow around dirt or debris particles, with dirt accumulating in the filter there is a gradual increase in pressure drop, collapsing of dirt piles is avoided or at least largely reduced (monitoring the pressure build-up may guide the user towards back flushing before the filter is block completely), and back flushing is supported by a kind of funnel behavior of the layered structure.

Referring now in greater detail to the drawings, FIG. 1 depicts a general schematic of a liquid separation system 10. A pump 20 receives a mobile phase from a solvent supply 25, typically via a degasser 27, which degases and thus reduces the amount of dissolved gases in the mobile phase. The pump 20—as a mobile phase drive—drives the mobile phase through a separating device 30 (such as a chromatographic column) comprising a stationary phase. A sampling unit 40 (having a needle/seat arrangement depicted in FIG. 1 schematically) is provided between the pump 20 and the separating device 30 in order to subject or add (often referred to as sample introduction) a sample fluid into the mobile phase. The stationary phase of the separating device 30 is configured for separating compounds of the sample liquid. A detector 50 is provided for detecting separated compounds of the sample fluid. A fractionating unit 60 can be provided for outputting separated compounds of sample fluid.

While the mobile phase can be comprised of one solvent only, it may also be mixed from plural solvents. Such mixing might be a low pressure mixing and provided upstream of the pump 20, so that the pump 20 already receives and pumps the mixed solvents as the mobile phase. Alternatively, the pump 20 might be comprised of plural individual pumping units, with plural of the pumping units each receiving and pumping a different solvent or mixture, so that the mixing of the mobile phase (as received by the separating device 30) occurs at high pressure and downstream of the pump 20 (or as part thereof). The composition (mixture) of the mobile phase may be kept constant overtime, the so called isocratic mode, or varied over time, the so called gradient mode.

A data processing unit 70, which can be a conventional PC or workstation, might be coupled (as indicated by the dotted arrows) to one or more of the devices in the liquid separation system 10 in order to receive information and/or control operation. For example, the data processing unit 70 might control operation of the pump 20 (e.g. setting control parameters) and receive therefrom information regarding the actual working conditions (such as output pressure, flow rate, etc. at an outlet of the pump). The data processing unit 70 might also control operation of the solvent supply 25 (e.g. setting the solvent/s or solvent mixture to be supplied) and/or the degasser 27 (e.g. setting control parameters such as vacuum level) and might receive therefrom information regarding the actual working conditions (such as solvent composition supplied over time, flow rate, vacuum level, etc.). The data processing unit 70 might further control operation of the sampling unit 40 (e.g. controlling sample injection or synchronization sample injection with operating conditions of the pump 20). The separating device 30 might also be controlled by the data processing unit 70 (e.g. selecting a specific flow path or column, setting operation temperature, etc.), and send—in return—information (e.g. operating conditions) to the data processing unit 70. Accordingly, the detector 50 might be controlled by the data processing unit 70 (e.g. with respect to spectral or wavelength settings, setting time constants, start/stop data acquisition), and send information (e.g. about the detected sample compounds) to the data processing unit 70. The data processing unit 70 might also control operation of the fractionating unit 60 (e.g. in conjunction with data received from the detector 50) and provides data back.

FIG. 1 schematically shows filters 200 at various positions within the fluidic path of the liquid chromatography system 10. Particularly, as shown schematically in FIG. 1, filters 200 according to exemplary embodiments may be provided at an inlet and an outlet of the separation column 30, at an outlet of the pump 20, at the sample injector 40. However, other positions for the filters 200 are possible as well.

FIG. 1 furthermore shows a back flush pump 95 configured for back flushing the filters 200 assigned to the separation column 30 when loaded with debris. To activate the back flushing procedure, switches 33, 35 are switched so that the separation column 30 is back flushed with fluid pumped by the back flush pump 95 in a direction opposite to an ordinary fluid flow direction 202 according to which the fluid is pumped during normal operation (i.e. a sample separation mode) of the liquid chromatography system 10. In other words, fluid is pumped by pump 20 along the ordinary fluid flow direction 202 (i.e. from inlet 91 to outlet 93) during separating components of the fluid, and fluid is pumped by back flush pump 95 backwards and opposite to the ordinary fluid flow direction 202 (i.e. from outlet 93 to inlet 91) during a back flushing mode for cleaning the respective filters 200 according to an embodiment of the invention.

FIG. 2 shows a fluidic member 204 which has a fluid inlet port 254 through which a liquid sample having some debris in it may flow towards a fluid outlet port 256. The flowing direction is indicated by reference numeral 202. The fluid inlet channel 254 is formed within a first housing part 250, whereas the fluid outlet channel 256 is formed within a second housing part 252. Between the first housing part 250 and the second housing 252, a gap is provided in which a filter 200 according to an exemplary embodiment of the invention is accommodated.

The filter 200 is configured for filtering debris such as wear or abrasion particles or other technical impurities out of the liquid flowing along the fluid flow direction 202 within the fluidic member 204. The filter comprises a first filter structure 206, a second filter structure 208 and a third filter structure 210 which are stacked and integrally formed along the fluid flow direction 202. Each of the filter structures 206, 208, 210 has an assigned defined pore size. In other words, pores 271 surrounded by matrix material 273 in the first filter portion 206 have a first size $d_1$, pores 275 surrounded by matrix material 277 in the adjacent second filter structure 208 have a second pore size $d_2$ and pores 279 surrounded by matrix material 281 in the third filter structure 210 have a third size $d_3$ (see detailed view 255 in FIG. 2). The first size $d_1$ is larger than the second size $d_2$, and the second size $d_2$ is larger than the third size $d_3$. Therefore, the defined pore sizes $d_1$, $d_2$, $d_3$ of the stacked filter structures 206, 208, 210 decreases along the fluid flow direction 202. This has the consequence that the liquid which flows along the liquid flow direction 202 is filtered first in the first filter structure 206 having the largest pores 271, so that the largest particles of debris only are trapped here. The remainder of the liquid including some remaining smaller debris will further propagate towards the middle filter structure 208 in which larger ones of the remaining debris particles are filtered out. In the third filter structure 210 with the smallest pores 279, the smallest debris particles are then filtered out so that a selective sorting and filtering of debris with regard to debris dimension is carried out by the filter 200. The filter structure 206, 208, 210 are metal layers with a pattern of pores 271, 275, 279 which are bonded together in a sintering process so as to form an integral structure. Each of the filter structures 206, 208, 210 can be realized as a disk-shaped or cylindrical plate. The pellet-like arrangement of the filter structures 206, 208, 210 can then be inserted (for instance adhered into) an angular support structure 220. Therefore, a tangible member is formed from components 206, 208, 210, 220.

In the embodiment of FIG. 2, the pores 271 in the first filter structure 206 have a dimension of 30 μm, the pores 275 in the second filter structure 208 have a dimension of 10 μm, and the pores 279 in the third layer structure 210 have a dimension of 2 μm.

The arrangement of FIG. 2 may be implemented, for instance, as a filter at an outlet of a sample injector of a liquid chromatography apparatus or as a filter at an inlet of a separation column of a liquid chromatography apparatus.

FIG. 3 shows a fluidic member 300 according to another exemplary embodiment of the invention. Fluid is introduced into the member 300 via a fluid inlet channel 320 formed in a first housing part 322. A second housing part 324 is attached to the first housing part 322 and has a fluid outlet channel 326 through which the fluid is to be guided. The housing parts 322, 324 enclose a hollow space which is filled with a filter 200 according to another exemplary embodiment of the invention. In the embodiment of FIG. 3, again three (any other number is possible) filter structures 306, 308, 310 are connected to one another to form an integral structure having a pore size sequence which monotonically decreases along the fluid flow direction, i.e. decreases along a direction of a fluid flowing from the fluid inlet channel 320 to the fluid outlet channel 326 via the filter 200. The three layer structures 306, 308 and 310 are all formed as cup-shaped elements which are stacked into one another with a concentrical axis. Therefore, the fluid exiting the end of the fluid inlet channel 320 will propagate through the cup-shaped filter 200 and will therefore be efficiently filtered.

The arrangement of FIG. 3 may be implemented, for instance, as a filter at an outlet of a mobile phase drive (i.e. a high pressure pump) of a liquid chromatography apparatus.

FIG. 4 shows a filter 200 according to yet another exemplary embodiment of the invention. Here, a fluidic path is defined by a plate 400 together with a recessed plate 402 arranged parallel to one another. The gap formed between the plates 400, 402 constitutes a fluid inlet channel 404. A fluid outlet channel is defined by recess 406 within the recessed plate 402. Between the fluid inlet channel 404 and the fluid outlet channel 406, filter 200 is sandwiched. This filter 200 is formed of only two layer structures, i.e. a first layer structure 410 and a second layer structure 408, the first layer structure 410 having larger pores than the pores of the second filter structure 408. The flow direction is here from first layer structure 410 to second layer structure 408.

Generally, different embodiments of the invention may implemented using very different values of numbers of the layer structures connected to form a filter. For instance, this number may be in a range between 2 and 20, more particularly between 2 and 8. In some embodiments, 3, 4 or 5 layer structures are connected to form a filter.

Figure 5A:
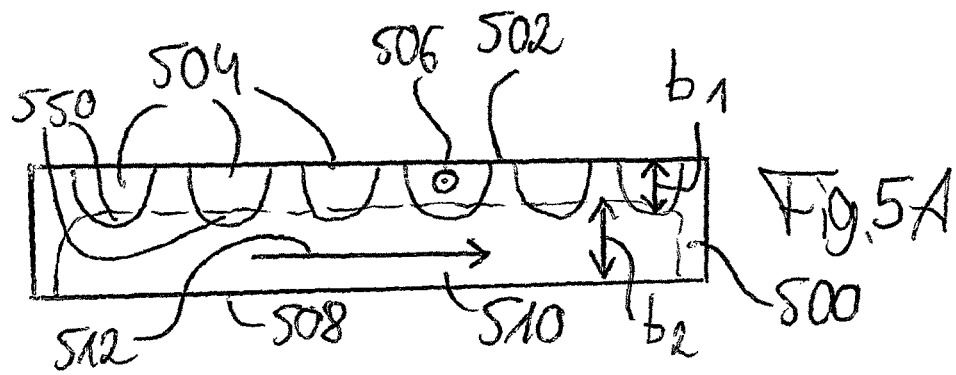
FIG. 5A shows a cross-sectional view.
Figure 5B:
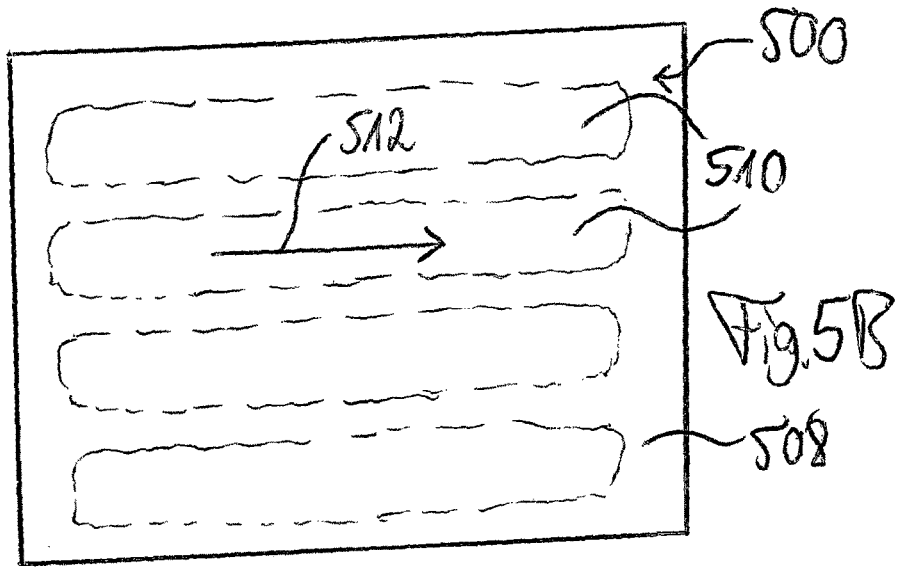
FIG. 5B shows a top plan view and FIG. 5C shows a bottom plan view of a filter structure for a filter according to an exemplary embodiment of the invention with a regular pattern of pores of a defined pore size.
Figure 5C:
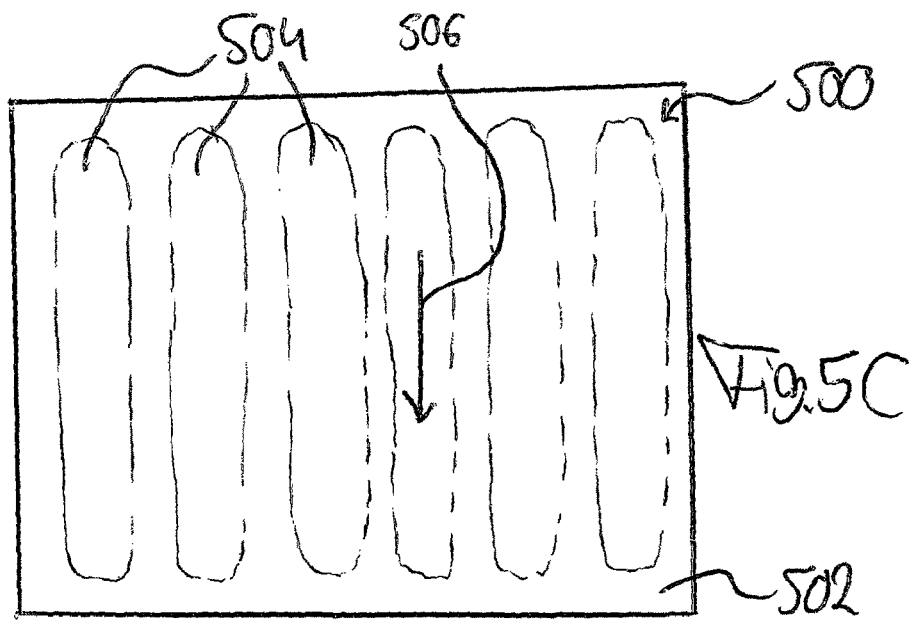

FIG. 5A to FIG. 5C illustrate how a layer structure as a basis for a filter can be formed which has pores of only one exactly defined size within this layer structure.

FIG. 5A shows a cross-section through a substrate 500 such as a metallic plate in which corresponding pores are formed. Also an electrical insulator or a semiconductor substrate may be used.

FIG. 5B shows a bottom plan view of a lower main surface 508 of the substrate 500.

FIG. 5C shows a top plan view of a top main surface 502 of the substrate 500.

As can be taken from FIG. 5A, the top main surface 502 of the substrate 500 is provided with a plurality of oblong first grooves 504 extending along a horizontal first direction 506, as also can be seen in FIG. 5C. The bottom main surface 508 of the substrate 500 which opposes the top main surface 502 is provided with a plurality of oblong second grooves 510 which extend along a second direction 512 being also horizontal, see FIG. 5B. The first direction 506 and the second direction 512 are essentially perpendicular to one another.

The first grooves 504 and the second grooves 510 have such a depth $b_1$, $b_2$ respectively within the substrate 500 that they form an array of through holes 550 in the substrate 500 at intersections between the first grooves 504 and the second grooves 510. Hence, the through holes 550 constitute the pores with the defined pore size. As can be taken particularly from FIG. 5A, the grooves 504, 510 have a concave shape so that the pores are defined by an intersection of the bottom portions of the concave shaped grooves 504, 510 only.

The grooves 504, 510 can be formed by a patterning and etching procedure using conventional masks. The depths $b_1$, $b_2$ of the grooves 504, 510 are in the order of magnitude of 10 μm so that very simple lithographic procedures can be implemented.

After having manufactured multiple sheets of the type as shown in FIG. 5A to FIG. 5C, however with different pore sizes, these different sheets are connected to one another for instance by glueing, welding, thermal bonding or sintering. For example, the metallic substrates 500 may be heated close to or above their melting point so that the surfaces of the respective substrates 500 already start melting. In this condition, the patterned substrates 500 may be pressed together for bonding and may be subsequently cooled, thereby forming an integral filter according to an exemplary embodiment of the invention.

FIG. 6A, FIG. 6B and FIG. 6C show three such correspondingly processed plates 602, 622 and 642 with pores 600, 620 and 640. Connecting the three plates 602, 622 and 642 to one another forms a filter part with a rectangular outer shape.

FIG. 7 shows a filter of another embodiment of the invention in which three filter structures 206, 208, 210 are serially stacked along a hydraulic flow direction with pore sizes $p_1 > p_2 > p_3$, each layer structure 206, 208, 210 having exactly one defined uniform pore size $p_1$, $p_2$ and $p_3$, respectively. Therefore, a sort of funnel architecture 700 with regard to the filtering performance can be obtained.

Figure 8A:
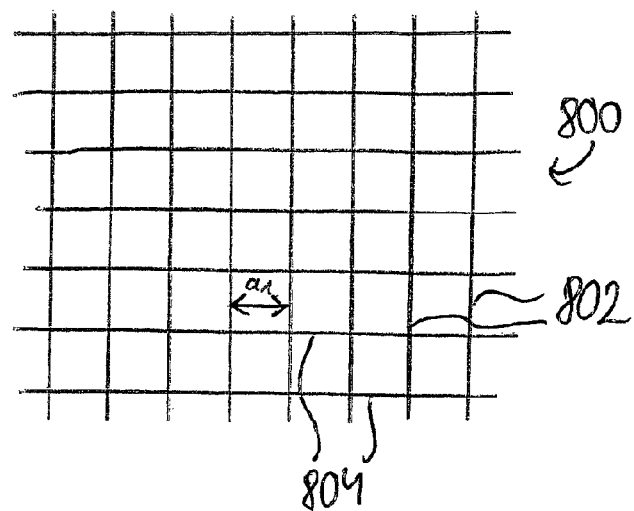
FIG. 8A shows a mesh with a large mesh aperture.
Figure 8B:
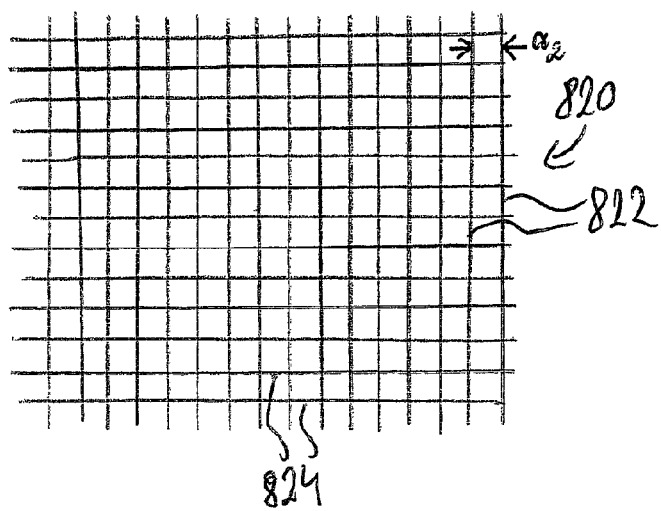
FIG. 8B shows a mesh with a medium mesh aperture.
Figure 8C:
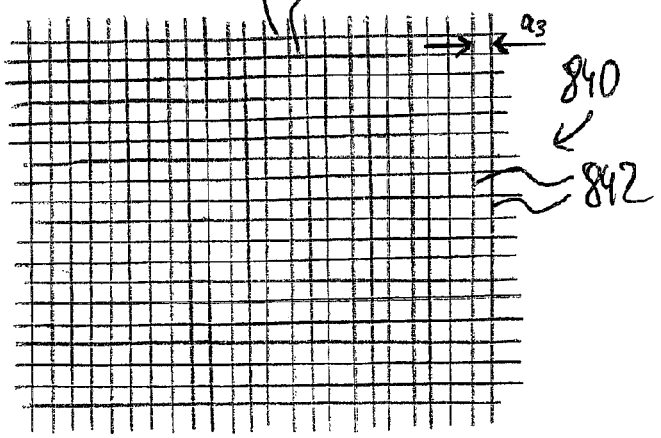
FIG. 8C shows a mesh with a small mesh aperture, wherein the meshes of FIG. 8A, FIG. 8B and FIG. 8C are connectable to one another so as to form a filter according to an exemplary embodiment of the invention.

FIG. 8A to FIG. 8C show meshes 800, 820, 840 defined by perpendicularly intersecting mesh wires 802, 804, 822, 824 and 842, 844, respectively. As can be taken from FIG. 8A, FIG. 8B, FIG. 8C, the mesh apertures $a_1 > a_2 > a_3$ of the meshes 800, 820, 840 are selected so that they differ from one another in view of different distances between adjacent wires 802/804, 822/824 and 842/844. Now connecting the meshes 800, 820, 840, for instance by thermal bonding, will generate a filter according to another exemplary embodiment of the invention with a defined monotonically decreasing pore size, if mesh 800 is arranged at an upstream end and mesh 840 is arranged at a downstream end of the filter relative to a flowing fluid, mesh 820 being sandwiched between meshes 800 and 840.

It should be noted that the term "comprising" does not exclude other elements or features and the "a" or "an" does not exclude a plurality. Also elements described in association with different embodiments may be combined. It should

The invention claimed is:

1. A filter for filtering debris out of a fluid flowing along a fluid flow direction in a fluidic member of a sample separation device, the filter comprising:
a plurality of filter structures, stacked along the fluid flow direction and each filter structure having voids with an exactly defined uniform void size for each filter structure;
wherein a plurality of the voids of each stacked filter structure comprises a substantially uniform diameter extending entirely through a thickness of each stack, with the uniform void size decreasing along the fluid flow direction from stack to stack in order to produce fraction-wise filtering of the debris with larger particles filtered out relatively early in the fluid flow direction through the stacked filter structure.

2. The filter according to claim 1, comprising at least one of the following features:
the plurality of filter structures are sheets connected to one another at main surfaces of adjacent sheets;
the plurality of filter structures are connected to one another as an integrally formed stack;
the plurality of filter structures comprise mesh wires, wherein different mesh wires have different mesh apertures forming the voids;
the plurality of filter structures are cup-shaped with different sizes so that the stacked arrangement is formed by interleaving the cup-shaped filter structures of different sizes into one another;
the plurality of filter structures are disk-shaped and are stacked concentrically to form a cylindrical filter;
an annular support structure, wherein the plurality of filter structures are fastened within a recess in the annular support structure; and
a number of the plurality of filter structures is in a range between 2 and 20.

3. The filter according to claim 1, wherein the defined uniform void size of the stacked filter structures decreases from stack to stack monotonically along the fluid flow direction.

4. The filter according to claim 1, wherein the defined uniform void sizes of the stacked filter structures are in a range between 0.5 μm and 100 μm.

5. A filter for filtering debris out of a fluid flowing along a fluid flow direction in a fluidic member of a sample separation device, the filter comprising:
a plurality of filter structures, stacked along the fluid flow direction and each filter structure having voids with a defined uniform void size in each filter structure;
wherein the uniform void size decreases along the fluid flow direction from stack to stack in order to produce fraction-wise filtering of the debris with larger particles filtered out relatively early in the fluid flow direction through the stacked filter structure,
wherein at least a part of the plurality of filter structures comprises a substrate,
wherein a first main surface of the substrate comprises a plurality of oblong first grooves formed into the substrate and extending along a first direction;
wherein a second main surface of the substrate opposing the first main surface comprises a plurality of oblong second grooves formed into the substrate and extending along a second direction; and
wherein intersections of the first grooves and the second grooves at a depth within the substrate comprise an array of through holes in the substrate, the through holes constituting the voids with the defined uniform void size.

6. The filter according to claim 5, comprising at least one of the following features:
the first direction is essentially perpendicular to the second direction;
the first grooves are straight grooves;
the second grooves are straight grooves;
the first grooves are parallel to one another;
the second grooves are parallel to one another;
the first grooves and the second grooves of the same substrate have all the same shape and dimensions.

7. The filter according to claim 5, wherein the first grooves and/or the second grooves are concave grooves.

8. The filter according to claim 5, wherein grooves of different ones of the plurality of filter structures differ concerning at least one geometrical parameter.

9. The filter according to claim 1, wherein the plurality of filter structures are suitable for operation in a pressure range between 400 bar and 1200 bar.

10. The filter according to claim 1, wherein the defined uniform void size of the stacked filter structures decreases along the fluid flow direction so as to provide for a funnel-like filtering of the debris out of the fluid.

11. A fluidic member for processing a fluid flowing along a fluid flow direction in a sample separation device, the fluidic member comprising:
a fluid inlet at which the fluid to be processed is supplied;
a processing unit configured for processing the supplied fluid;
a fluid outlet at which the fluid is supplied after processing by the processing unit; and
at least one filter according to claim 1 for filtering debris out of the fluid and being arranged between the fluid inlet and the fluid outlet.

12. The fluidic member according to claim 11, configured as at least one of:
a separation unit configured for separating compounds of the fluid, wherein the filter is arranged at a fluid inlet and/or at a fluid outlet of the separation unit;
a mobile phase drive configured to drive the fluid, wherein the filter is arranged at a fluid outlet of the mobile phase drive;
a sample injector for injecting the fluid in a sample separation path, wherein the sample injector comprises an injection needle and a seat, wherein the injection needle is selectively insertable into the seat for conducting the fluid between the injection needle and the seat, wherein the injection needle is selectively movable out of the seat, and wherein the filter is arranged at a fluid outlet of the sample injector;
a metering pump for a sample injector for injecting the fluid in a sample separation path;
a detector configured to detect separated compounds of the fluid;
a collection unit configured to collect separated compounds of the fluid;
a degassing apparatus for degassing the fluid; and
a piston pump having a piston chamber and a piston configured for reciprocating within the piston chamber.

13. The fluidic member according to claim 11, comprising a back flush unit configured for back flushing the filter when loaded with debris, the back flush unit being configured for flushing the loaded filter with flush fluid flowing in an opposite direction compared to the fluid flow direction.

14. A sample separation device for separating compounds of a sample fluid in a mobile phase, the sample separation device comprising:
   a mobile phase drive configured to drive the mobile phase through the sample separation device,
   a separation unit configured for separating compounds of the sample fluid in the mobile phase, and
   a filter according to claim 1 for filtering debris out of at least one of the sample fluid and the mobile phase.

15. The sample separation device according to claim 14, further comprising at least one of:
   a metering pump for a sample injector for injecting the sample fluid in the mobile phase;
   a sample injector for injecting the sample fluid in the mobile phase, wherein the sample injector comprises an injection needle and a seat, wherein the injection needle is selectively insertable into the seat for conducting the sample fluid between the needle and the seat, and wherein the injection needle is selectively movable out of the seat;
   a detector configured to detect separated compounds of the sample fluid;
   a collection unit configured to collect separated compounds of the sample fluid;
   a degassing apparatus for degassing the mobile phase;
   a piston pump having a piston chamber and a piston configured for reciprocating within the piston chamber.

16. A filter for filtering debris out of a fluid flowing along a fluid flow direction in a fluidic member of a sample separation device, the filter comprising:
   a first housing part comprising a fluidic inlet port;
   a second housing part comprising a fluidic outlet port, the first housing part and the second housing port forming a hollow space therebetween when coupled together such that the fluid flows into the inlet port and out of the outlet port;
   a plurality of filter structures stacked along the fluid flow direction in the hollow space, each filter structure having voids with an exactly defined uniform void size for each filter structure;
   wherein a plurality of the voids of each stacked filter structure comprises a substantially uniform diameter extending entirely through each stack, with the uniform void size decreasing along the fluid flow direction from stack to stack in order to produce fraction-wise filtering of the debris with larger particles filtered out relatively early in the fluid flow direction through the stacked filter structure.

* * * * *